(12) United States Patent
Casci et al.

(10) Patent No.: US 11,400,439 B2
(45) Date of Patent: Aug. 2, 2022

(54) JMZ-1S, A CHA-CONTAINING MOLECULAR SIEVE AND METHODS OF PREPARATION

(71) Applicant: JOHNSON MATTHEY PUBLIC LIMITED COMPANY, London (GB)

(72) Inventors: John Casci, Billingham (GB); Paul Cox, Portsmouth (GB); Alessandro Turrina, Billingham (GB)

(73) Assignee: Johnson Matthey Public Limited Company, London (GB)

( * ) Notice: Subject to any disclaimer, the term of this patent is extended or adjusted under 35 U.S.C. 154(b) by 110 days.

(21) Appl. No.: 16/817,732

(22) Filed: Mar. 13, 2020

(65) Prior Publication Data

US 2020/0316574 A1    Oct. 8, 2020

Related U.S. Application Data

(60) Provisional application No. 62/818,259, filed on Mar. 14, 2019.

(51) Int. Cl.

| | | |
|---|---|---|
| *B01J 29/85* | (2006.01) | |
| *B01D 53/94* | (2006.01) | |
| *B01J 35/04* | (2006.01) | |
| *B01J 37/00* | (2006.01) | |
| *B01J 37/03* | (2006.01) | |
| *B01J 37/04* | (2006.01) | |
| *B01J 37/08* | (2006.01) | |
| *B01J 37/30* | (2006.01) | |
| *C01B 39/54* | (2006.01) | |
| *C07C 1/24* | (2006.01) | |
| *C01B 39/04* | (2006.01) | |
| *C01B 39/48* | (2006.01) | |
| *C01B 39/10* | (2006.01) | |
| *C01B 39/06* | (2006.01) | |
| *B01J 29/70* | (2006.01) | |
| *B01J 29/76* | (2006.01) | |
| *C01B 39/46* | (2006.01) | |

(52) U.S. Cl.
CPC .......... *B01J 29/85* (2013.01); *B01D 53/9418* (2013.01); *B01J 29/7015* (2013.01); *B01J 29/763* (2013.01); *B01J 35/04* (2013.01); *B01J 37/0018* (2013.01); *B01J 37/031* (2013.01); *B01J 37/036* (2013.01); *B01J 37/04* (2013.01); *B01J 37/08* (2013.01); *B01J 37/30* (2013.01); *C01B 39/04* (2013.01); *C01B 39/06* (2013.01); *C01B 39/10* (2013.01); *C01B 39/48* (2013.01); *C01B 39/54* (2013.01); *C07C 1/24* (2013.01); *B01D 53/9436* (2013.01); *B01D 2255/10* (2013.01); *B01D 2255/2045* (2013.01); *B01D 2255/2065* (2013.01); *B01D 2255/20761* (2013.01); *B01D 2255/50* (2013.01); *B01D 2255/9155* (2013.01); *C01B 39/065* (2013.01); *C01B 39/46* (2013.01); *C01P 2002/72* (2013.01); *C01P 2004/03* (2013.01); *C07C 2523/72* (2013.01); *C07C 2523/83* (2013.01); *C07C 2529/85* (2013.01)

(58) Field of Classification Search
CPC ...... B01J 29/85; B01J 29/763; B01J 29/7015; B01J 35/04; B01J 37/0018; B01J 37/031; B01J 37/036; B01J 37/04; B01J 37/08; B01J 37/30; C01B 39/04; C01B 39/06; C01B 39/065; C01B 39/10; C01B 39/46; C01B 39/48; C01B 39/54; B01D 53/9418; B01D 53/9436; B01D 2255/10; B01D 2255/2045; B01D 2255/2065; B01D 2255/50; B01D 2255/20761; B01D 2255/9155; C01P 2002/03; C01P 2002/72; C01P 2004/03; C07C 2523/72; C07C 2523/83; C07C 2523/85
USPC ........ 502/60, 62, 73, 74, 214; 423/700, 701, 423/702, 703, 704, 705, 706, 713, 718
See application file for complete search history.

(56) References Cited

U.S. PATENT DOCUMENTS

| | | | | |
|---|---|---|---|---|
| 4,440,871 | A * | 4/1984 | Lok | ........................ C07C 5/2716 502/214 |
| 4,544,538 | A | 10/1985 | Zones | |
| 2003/0232006 | A1 | 12/2003 | Cao et al. | |
| 2004/0253163 | A1 | 12/2004 | Cao et al. | |
| 2007/0043249 | A1 | 2/2007 | Cao et al. | |
| 2009/0018379 | A1 | 1/2009 | Cao et al. | |
| 2010/0022721 | A1 | 1/2010 | Mertens | |
| 2012/0316312 | A1* | 12/2012 | Mertens | ................... B01J 29/85 526/351 |
| 2013/0323164 | A1* | 12/2013 | Feyen | ................... B01J 29/763 423/704 |

FOREIGN PATENT DOCUMENTS

| | | |
|---|---|---|
| CN | 101481121 A | 7/2009 |
| CN | 103663492 A | 3/2014 |

(Continued)

OTHER PUBLICATIONS

Lok et al., "Silicoaluminophosphate Molecular Sieves: Another New Class of Microporous Crystalline Inorganic Solids," J. Am Chem. Soc. 1984 (106) pp. 6092-6093.

*Primary Examiner* — Elizabeth D Wood

(57) ABSTRACT

JMZ-1S, a silicoaluminophosphate molecular sieve having a CHA structure and containing a trimethyl(cyclohexylmethyl)ammonium cation cation is described. A calcined product, JMZ-1SC, formed from JMZ-1S is also described. Methods of preparing JMZ-1S, JMZ-1SC and metal containing calcined counterparts of JMZ-1SC are described along with methods of using JMZ-1SC and metal containing calcined counterparts of JMZ-1SC in treating exhaust gases and in converting methanol to olefines.

31 Claims, 3 Drawing Sheets

(56) References Cited

FOREIGN PATENT DOCUMENTS

| | | | |
|---|---|---|---|
| CN | 104150504 A | | 11/2014 |
| EP | 0103117 | * | 3/1984 |
| WO | 2013114172 A1 | | 8/2013 |
| WO | 2013/182974 | * | 12/2013 |
| WO | 2017133301 A1 | | 8/2017 |

* cited by examiner

JMZ-1S, A CHA-CONTAINING MOLECULAR SIEVE AND METHODS OF PREPARATION

FIELD OF INVENTION

The present invention relates to a JMZ-1S, a CHA-containing silicoaluminophosphate (SAPO) molecular sieve containing a trimethyl(cyclohexylmethyl)ammonium cation, and a calcined product (JMZ-1SC) formed from JMZ-1S. The invention also relates to methods of preparation of JMZ-1S and JMZ-1SC and methods using the calcined product formed from JMZ-1S as a catalyst.

BACKGROUND OF THE INVENTION

Molecular sieves are a class of crystalline materials with defined arrangements of cavities, channels and/or pores. The molecular sieve framework or topology is characteristic of the specific type of molecular sieve. A framework type or topological type is unique and is provided with a unique three letter code by the IZA (International Zeolite Association), which maintains a full listing of framework types at http://www.iza-structure.org/data-bases/. Framework types or topological types are not only defined by composition, but also by the arrangement of the atoms that bound the cavities, channels and/or pores that make up the structure. Molecular sieves can usually be identified by their x-ray diffraction (XRD) pattern.

In general, aliovalent substitutions of Al and P in an aluminophosphate (AlPO) are possible: substitution of Al with a metal cation provides metalloaluminophosphates (MAPOs) and substitution of P with Si gives a silicoaluminophosphate (SAPO). Metal silicoaluminophosphates (MSAPOs) can be formed with metals and silica.

For example, the framework type (topological type) CHA gets its designation from the natural mineral chabazite. Synthetic versions of the CHA topological type have been described, such as SSZ-13 (U.S. Pat. No. 4,544,538). SSZ-13 has a silica:alumina compositional ratio that differs from that of the natural mineral. SAPO-34 (Lok et al., 1984, J. Am. Chem. Soc., 106, 6092) is another example of a CHA topological type. Since this has a framework composition consisting of $SiO_2$, $AlO_2$ and $PO_2$ tetrahedra, it is a SAPO and not an aluminosilicate.

Chabazite, SSZ-13 and SAPO-34 all have the same framework structure (topological type) but have different compositions. The compositional differences have a profound influence on properties and therefore affect utility in industrial applications.

Molecular sieves are commercially important and have several industrial applications particularly in catalysis and as adsorbents. Zeolites of certain frameworks like CHA are known to be effective as catalysts in diverse applications such as for treating combustion exhaust gas, e.g. in control of nitrogen oxide NOx emission and in catalytic conversion of methanol to olefins among others.

Zeolites and SAPOs are two kinds of molecular sieves. Zeolites have traditionally been considered as crystalline or quasi-crystalline aluminosilicates having repeating TO4 tetrahedral units. The tetrahedrally-coordinated atoms T are usually Al and Si, though examples with P, B, Fe and Ga are also known. The tetrahedral units are connected to form the framework. Various synthetic zeolites are known. In AlPOs with Al:P of 1:1, a zeolite-like framework structure is found in which each Al is bonded to four phosphate tetrahedra. On the other hand, SAPOs typically have a three-dimensional microporous crystalline framework of $PO_2^+$, $AlO_2^-$ and $SiO_2$ tetrahedral units.

Most Al cations in an aluminophosphate have four-fold coordination, though it is also possible for them to bind additional ligands such as water, fluoride or hydroxide ions if these are present in the reaction mixture. Where positively-charged SDAs are used, negatively charged ligands can act to balance the positive charge from the SDA. Heating the framework to remove the SDA molecules also removes the additional ligands.

Since an aluminophosphate ($AlPO_4$) framework is inherently neutral, the incorporation of silicon into the $AlPO_4$ framework by substitution generates an overall negative charge. As with aluminosilicate zeolites, this can be used to generate acid sites. The number and location of silicon atoms incorporated into an $AlPO_4$ framework can thus be used to tailor the catalytic properties of a given SAPO.

Most of the framework types described by the IZA require a structure directing agent (SDA), also referred to as a "template" or "templating agent" to facilitate their synthesis. With very few exceptions, the SDA is incorporated into the molecular sieve framework during the synthesis process and must be removed, usually by a heat treatment stage, before the cavities, channels and/or pores can be made available and accessible to other molecules.

In typical synthesis techniques, solid zeolite crystals precipitate from a reaction mixture which contains the framework reactants (e.g., a source of silica and a source of alumina), a source of hydroxide ions (e.g., NaOH), and an SDA. Such synthesis techniques usually take several days (depending on factors such as crystallization temperature) to achieve the desired crystallization. When crystallization is complete, the solid precipitate containing the zeolite crystals is separated from the mother liquor which is discarded. This discarded mother liquor contains unused SDA, which is often degraded due to harsh reaction conditions, and unreacted silica.

There is a need to develop new molecular sieves having the basic structure of known zeolites, where minor changes in the structure can affect one or more of the catalytic properties of the molecular sieve. In some cases, while minor changes in the structure may not be discernable using normally used analytical techniques, the catalytic activity of the structurally modified molecular sieves may be improved relative to very closely related analogous molecular sieves.

Unexpected improvements in the catalytic activity of such structurally modified molecular sieves can allow for the compositions of exhaust gases from engines to meet various regulatory requirements.

Such modifications in the structure of molecular sieves may also promote the formation of methylamines from the reaction of methanol and ammonia and the conversion of methanol to lower olefins, especially ethylene and propylene in processes known as conversion of methanol to an olefin (MTO) and an oxygenate to olefin (OTO).

SUMMARY OF THE INVENTION

In a first aspect of the invention, provided is a novel SAPO, JMZ-1S, comprising a CHA structure and containing trimethyl(cyclohexylmethyl)ammonium cation.

In another aspect of the invention, provided is a calcined product (JMZ-1SC) formed from JMZ-1S.

In a second aspect of the invention, provided is a method for forming JMZ-1S by using trimethyl(cyclohexylmethyl) ammonium cation as a structure directing agent.

In a third aspect of the invention, provided is a method for forming JMZ-1SC by calcining JMZ-1S.

In a fourth aspect of the invention, provided is a method for treating an exhaust gas from an engine by contacting the exhaust gas with JMZ-1SC or a metal impregnated JMZ-1SC.

In a fifth aspect of the invention, provided is a method of converting methanol to an olefin (MTO) by contacting methanol with a calcined molecular sieve of the first or second aspect of the invention.

DETAILED DESCRIPTION OF THE INVENTION

As used in this specification and the appended claims, the singular forms "a", "an" and "the" include plural referents unless the context clearly indicates otherwise. Thus, for example, reference to "a catalyst" includes a mixture of two or more catalysts, and the like.

The term "calcine", or "calcination", means heating the material in air or oxygen. This definition is consistent with the IUPAC definition of calcination. (IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook.) Calcination is performed to decompose a metal salt and promote the exchange of metal ions within the catalyst and also to adhere the catalyst to a substrate. The temperatures used in calcination depend upon the components in the material to be calcined and generally are between about 400° C. to about 900° C. for approximately 1 to 8 hours. In some cases, calcination can be performed up to a temperature of about 1200° C. In applications involving the processes described herein, calcinations are generally performed at temperatures from about 400° C. to about 700° C. for approximately 1 to 8 hours, preferably at temperatures from about 400° C. to about 650° C. for approximately 1 to 4 hours.

The term "about" means approximately and refers to a range that is optionally ±25%, preferably ±10%, more preferably, ±5%, or most preferably ±1% of the value with which the term is associated.

When a range, or ranges, for various numerical elements are provided, the range, or ranges, can include the values, unless otherwise specified.

Figure 3:
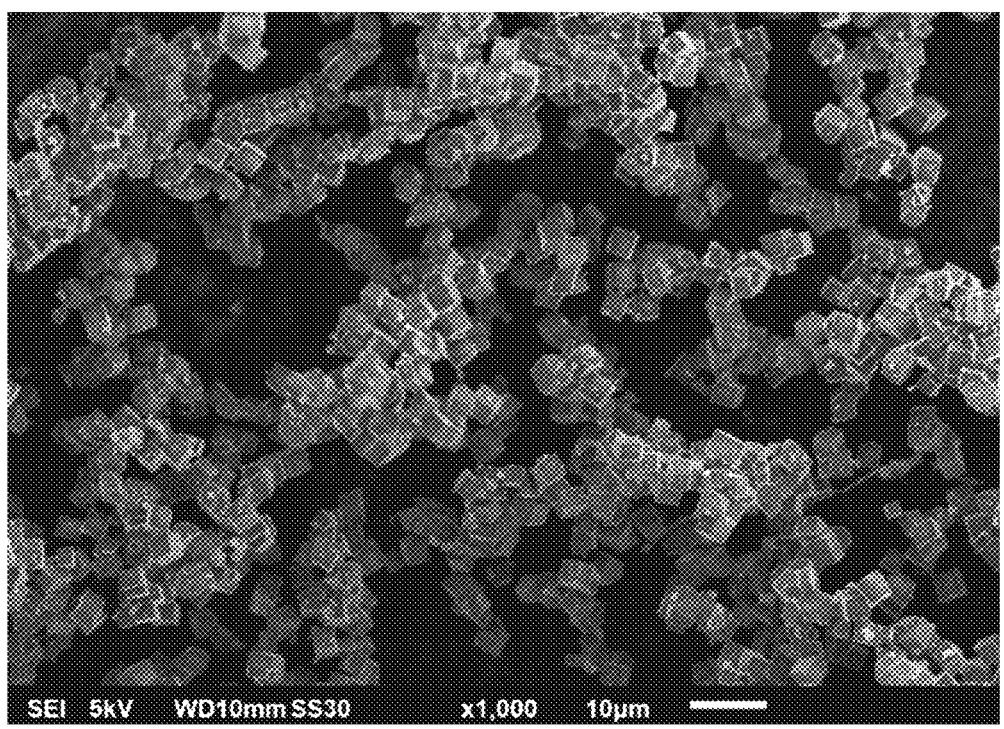
FIG. 3 is an XRD spectra of a sample of JMZ-1S as prepared in Example 3.
Figure 4:
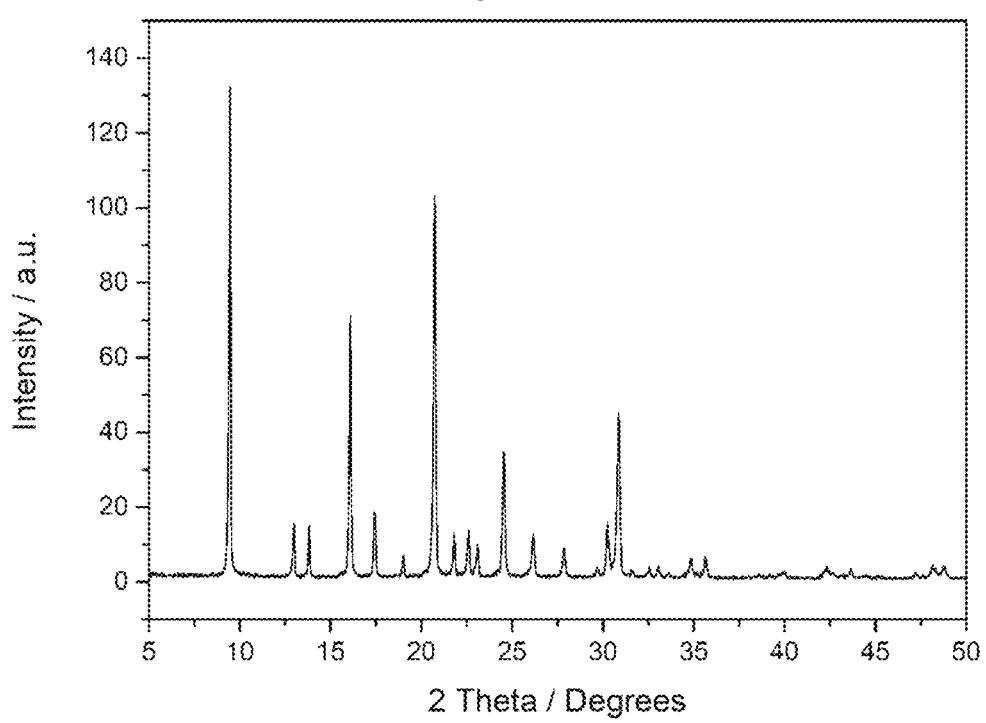
FIG. 4 is an SEM micrograph of a sample of JMZ-1S as prepared in Example 3.

In a first aspect of the invention, provided is a novel silicoaluminophosphate molecular sieve, JMZ-1S, comprising a CHA structure and containing trimethyl(cyclohexylmethyl)ammonium cation. The powder XRD of JMZ-1S is shown in FIG. 3. The characteristic lines are shown in Table I.

TABLE I

Powder XRD characteristic lines for as-made (template containing) JMZ-1S molecular sieve.

| Degrees two-theta | I/Io |
|---|---|
| 9.47 | VS |
| 12.99 | W |
| 13.80 | W |
| 16.09 | S |
| 17.39 | W |
| 18.99 | W |
| 20.74 | VS |
| 21.78 | W |
| 22.61 | W |
| 23.09 | W |
| 24.49 | M |
| 26.16 | W |
| 27.84 | W |
| 30.20 | W |
| 30.85 | M |
| 34.84 | W |
| 35.61 | W |

(a) = ±0.2

The relative intensity is based on the strongest line in the X-ray pattern which is assigned a value of 100. W (weak) is less than 20; M (medium) is between 20 and 40; S (strong) is between 40 and 60; and VS (very strong) is greater than 60.

The X-ray powder diffraction patterns were determined by standard techniques. The radiation was the K-alpha/doublet of copper and a scintillation counter spectrometer with a strip-chart pen recorder was used. The peak heights I and their positions, in degrees, 2θ, where θ is the Bragg angle, were read from the spectrometer chart. From these measured values, the relative intensities, 100 $I/I_0$, where $I_0$ is the intensity of the strongest line or peak, and d, the interplanar spacing in Angstroms corresponding to the recorded lines, can be calculated. The X-ray diffraction pattern of Table 1 is characteristic of all species of JMZ-1S family compositions. Minor variations in the diffraction pattern in the tables or FIGS. 1-4 and 6 can also result from variations in the organic compound used in the preparation and from variations in the silica-to-alumina mole ratio from sample to sample. Notwithstanding these minor perturbations, the basic crystal structures for the as-prepared condition and the calcined condition remain substantially unchanged.

In another aspect of the invention, provided is a calcined product (JMZ-1SC) formed from calcining JMZ-1S. The calcined product can be synthesized by the methods described herein and preferably has a $SiO_2/Al_2O_3$ (SAR) of between 0 and 0.65, inclusive, preferably about 0.3 to about 0.6, more preferably about 0.45 to about 0.55 and a $P_2O_5/Al_2O_3$ (PAR) ratio of between 0.65 and 1.0 inclusive, preferably about 0.7 to about 0.9, more preferably about 0.75 to about 0.85. The SAR and PAR can be selectively achieved based on the composition of the starting synthesis mixture and/or adjusting other process variables. The SAR and PAR of the SAPO may be determined by conventional analysis. This ratio is meant to represent, as closely as possible, the ratio in the rigid atomic framework of the SAPO crystal and to exclude silicon or aluminum or phosphorous in the binder (for catalyst applications) or, in cationic or other form, within the channels.

The XRD spectra of the calcined product is similar to other zeolites having a CHA type structure.

In yet another aspect of the invention, provided is a method for forming JMZ-1S by using a trimethyl(cyclohexylmethyl)ammonium cation as a structure directing agent. The method comprises the sequential steps of (a) forming a CHA topological type SAPO reaction mixture and (b) reacting the mixture under crystallization conditions (24 hours at 210° C. while rotating the reactor at 45 rpm) to form crystals containing an SDA and having an x-ray diffraction pattern consistent with that of JMZ-1S. The precipitated SAPO crystals are preferably separated from the subsequent mother liquor by any conventional technique, such as filtration.

As used herein, the term "CHA" refers to a CHA topological type as recognized by the International Zeolite Association (IZA) Structure Commission and the term "CHA zeolite or zeotype" means an aluminosilicate or aluminophosphate in which the primary crystalline phase is CHA. Other crystalline phases may also be present, but the primary crystalline phase comprises at least about 90 weight percent CHA, preferably at least about 95 weight percent CHA, and even more preferably at least about 97 or at least about 99 weight percent CHA. Preferably, the CHA molecular sieve is substantially free of other crystalline phases and is not an intergrowth of two or more framework types. By "substantially free" with respect to other crystalline phases, it is meant that the molecular sieve contains at least 99 weight percent CHA.

As used herein the term "SAPO" means a synthetic silicoaluminophosphate molecular sieve having a framework constructed of alumina, silica and phosphorus (i.e., repeating $SiO_4$, $AlO_4$ and $PO_4$ tetrahedral units).

The reaction mixture for the JMZ-1S synthesis process typically contains at least one source of phosphorous, at least one source of alumina, at least one source of silica and at least one SDA useful in forming JMZ-1S. A number of aluminum compounds and their mixtures are suitable for use as the aluminum component in the present invention. A source of alumina can comprise for example an aluminum alkoxide, such as aluminum isopropoxide, aluminum tri-ethoxide, aluminum tri-n-butoxide and aluminum tri-isobutoxide, an aluminum oxide, an aluminum phosphate, aluminum hydroxide, sodium aluminate, (pseudo)boehmite, hydrated alumina, organoalumina, aluminum hydroxy chloride, colloidal alumina, and mixtures thereof. Preferably, the aluminum component comprises a material selected from the group consisting of aluminum hydroxide, boehmite and pseudoboehmite, most preferably aluminum hydroxide. A source of phosphorus can comprise, but is not limited to, orthophosphoric acid, phosphorus acid, phosphoric acid, organic phosphate such as triethyl phosphate and trimethylphosphate, aluminophosphate, and mixtures thereof. Preferred is a source of phosphorus comprising a material selected from the group consisting of phosphoric acid (such as the commercially available 85 wt % phosphoric acid in water), and orthophosphoric acid. Alternatively, phosphorus oxides ($P_2O_3$, $P_2O_4$, $P_2O_5$ and $POCl_3$) may be used, preferably after they are dissolved in a suitable solvent such as water.

A source of silica can comprise a number of silicon compounds and their mixtures. The silicon compounds include for example a silica sol, silica gel, tetraethyl silicate, tetramethyl silicate, silicon alkoxide, colloidal silica, silica gel, a silicate such as fumed silica, a tetraalkyl orthosilicate, or an aqueous colloidal suspension of silica, and mixtures thereof. Preferably the source of silica comprises a silicon component selected from the group consisting of silica sol, silica gel, colloidal silica, fumed silica, silicic acid, most preferably fumed silica.

A suitable organic template comprises trimethyl(cyclohexylmethyl)ammonium cation. The corresponding anions can be acetate, bicarbonate, bromide, carbonate, carboxylate, chloride, fluoride, hydroxide, iodide, sulfate and tetrafluoroborate, preferably hydroxide.

It is understood, however, that the synthesis method described herein is not necessarily limited to silicoaluminophosphates, but can also be applied to synthesize other molecular sieves having an CHA structure such as (but not limited to) magnesium or manganese or iron or cobalt or zinc aluminophosphate and silicoaluminophosphates, when aluminum is effectively replaced by Mg, Mn, Fe, Co or Zn. Different magnesium, manganese, iron, cobalt and zinc compounds and their mixtures are suitable for use as the magnesium, manganese, iron, cobalt and zinc component in the present invention. The magnesium, manganese, iron, cobalt and zinc compounds include, but are not limited to magnesium sulfate, magnesium fluoride, magnesium chloride, magnesium bromide, magnesium iodide, magnesium acetate, magnesium oxide, manganese (II) sulfate, manganese(II) fluoride, manganese(II) chloride, manganese(II) bromide, manganese(II) iodide, manganese(II) acetate, manganese(II) oxide, iron(II) oxalate, iron(II) chloride, iron(II) sulfate, iron(III) chloride, iron(III) nitrate, cobalt(II) sulfate, cobalt(II) fluoride, cobalt(II) chloride, cobalt(II) bromide, cobalt(II) iodide, cobalt(II) acetate, cobalt(II) oxide, zinc sulfate, zinc fluoride, zinc chloride, zinc bromide, zinc iodide, zinc acetate, zinc oxide.

Preferably, the overall process will have an overall yield on silica of at least about 60%, for example at least about 70%, at least about 80%. Preferably, the overall process will have an overall yield on SDA of at least about 40%, for example at least about 60%, at least about 80%, at least about 90%, about 40-90%, about 40-60%, about 60-80%, about 80-90%, about 90-95%, or about 95-99%.

The reaction mixture can be in the form of a solution, a colloidal dispersion (colloidal sol), gel, or paste, with a gel being preferred. JMZ-1S can be prepared from a reaction mixture having the composition shown in Table II. Aluminum-, phosphorous- and silicon-containing reactants are expressed as $Al_2O_3$, $P_2O_5$ and $SiO_2$ respectively.

TABLE II

|  | Typical | Preferred |
| --- | --- | --- |
| $P_2O_5/Al_2O_3$ | 0.5-1 | 0.9-1 |
| $SiO_2/Al_2O_3$ | 0.2-0.8 | 0.4-0.6 |
| $SDA/Al_2O_3$ | 0.1-1.50 | 0.8-1.20 |
| $H_2O/Al_2O_3$ | 20-200 | 80-120 |

Reaction temperatures, mixing times and speeds, and other process parameters that are suitable for conventional CHA synthesis techniques are also generally suitable for the present invention. Generally, the reaction mixture is maintained at an elevated temperature until the JMZ-1S crystals are formed. The hydrothermal crystallization is usually conducted under autogenous pressure, at a temperature between about 75-220° C., for example between about 180 and 210° C., for duration of several hours, for example, about 0.1-20 days, and preferably from about 0.25-3 days. Preferably, the SAPO is prepared using stirring or agitation.

During the hydrothermal crystallization step, crystals of JMZ-1S can be allowed to nucleate spontaneously from the reaction mixture. The use of JMZ-1S crystals or other crystals with CHA topology as seed material can be advantageous in decreasing the time necessary for complete crystallization to occur. When used as seeds, JMZ-1S crystals can be added in an amount between 0.1 and 10% of the weight of silica used in the reaction mixture.

Once the JMZ-1S crystals have formed, the solid product is separated from the reaction mixture by standard separation techniques such as filtration. The JMZ-1S crystals are water-washed and then dried, for several second to a few minutes (e.g., 5 second to 10 minutes for flash drying) or several hours (e.g., about 4-24 hours for oven drying at 75-150° C.), to obtain as-synthesized JMZ-1S crystals having a CHA topological type framework and an SDA within the crystals. The drying step can be performed at atmospheric pressure or under vacuum.

It will be appreciated that the foregoing sequence of steps, as well as each of the above-mentioned periods of time and temperature values are merely exemplary and may be varied.

The JMZ-1S crystals produced in accordance with this process can be uniform, with little to no twinning and/or multiple twinning or may form agglomerates.

The JMZ-1S crystals produced in accordance with the methods described herein can have a mean crystalline size of about 0.1 to about 50 µm, for example about 0.5 to about 25 µm, about 1 to about 15 µm, and about 1 to about 5 µm. Large crystals can be milled using a jet mill or other particle-on-particle milling technique to an average size of about 1.0 to about 1.5 micron to facilitate washcoating a slurry containing the catalyst to a substrate, such as a flow-through monolith.

In still another aspect of the invention, provided is a method for forming JMZ-1SC by calcining JMZ-1S.

JMZ-1SC, the SAPO molecular sieves formed by the calcination of JMZ-1S, is useful as a catalyst in certain applications. The dried JMZ-1S crystals are preferably calcined, but can also be used without calcination. JMZ-1SC can be used either without a post-synthesis metal exchange or with a post-synthesis metal exchange, preferably with a post-synthesis metal exchange. Thus, in certain aspects of the invention, provided is a catalyst comprising JMZ-1SC that is free or essentially free of any exchanged metal, particularly post-synthesis exchanged or impregnated metals. JMZ-1SC preferably can comprise one or more catalytic metal ions exchanged or otherwise impregnated into the channels and/or cavities of the SAPO. Examples of metals that can be post-synthesis exchanged or impregnated include transition metals, including copper, nickel, zinc, iron, tungsten, molybdenum, cobalt, titanium, zirconium, manganese, chromium, vanadium, niobium, as well as tin, bismuth, and antimony; noble metals including platinum group metals (PGMs), such as ruthenium, rhodium, palladium, indium, platinum, and precious metals such as gold and silver; alkaline earth metals such as beryllium, magnesium, calcium, strontium, and barium; and rare earth metals such as lanthanum, cerium, praseodymium, neodymium, europium, terbium, erbium, ytterbium, and yttrium. Preferred transition metals for post-synthesis exchange are base metals, and preferred base metals include those selected from the group consisting of manganese, iron, cobalt, nickel, copper and mixtures thereof.

The transition metal can be present in an amount of about 0.1 to about 10 weight percent, for example about 0.5 to about 5 weigh percent, about 0.1 to about 1.0 weight percent, about 2.5 to about 3.5 weight percent, and about 4.5 to about 5.5 weight percent, wherein the weight percent is relative to the total weight of the SAPO material.

Particularly preferred exchanged metals include copper and iron, particularly when combined with calcium and/or cerium and particularly when the transition metals ($T_M$) and the alkaline metals ($A_M$) are present in a $T_M:A_M$ molar ratio of about 15:1 to about 1:1, for example about 10:1 to about 2:1, about 10:1 to about 3:1, or about 6:1 to about 4:1, Metals incorporated post-synthesis can be added to the molecular sieve via any known technique such as ion exchange, impregnation, isomorphous substitution, etc.

These exchanged metal cations are distinct from metals constituting the molecular framework of SAPO molecular sieves, and thus metal exchanged SAPO molecular sieves are distinct from metal-substituted SAPO molecular sieves.

Where the catalyst is part of a washcoat composition, the washcoat may further comprise a binder containing Ce or ceria. When the binder contains Ce or ceria, the Ce containing particles in the binder are significantly larger than the Ce containing particles in the catalyst.

Catalysts of the present invention are particularly applicable for heterogeneous catalytic reaction systems (i.e., solid catalyst in contact with a gas reactant). To improve contact surface area, mechanical stability, and/or fluid flow characteristics, the catalysts can be disposed on and/or within a substrate, preferably a porous substrate. A washcoat containing the catalyst can be applied to an inert substrate, such as corrugated metal plate or a honeycomb cordierite brick. Alternatively, the catalyst is kneaded along with other components such as fillers, binders, and reinforcing agents, into an extrudable paste which is then extruded through a die to form a honeycomb brick. Accordingly, a catalyst article can comprise an CHA catalyst described herein coated on and/or incorporated into a substrate.

Certain aspects of the invention provide a catalytic washcoat. The washcoat comprising a calcined product formed from JMZ-1S described herein is preferably a solution, suspension, or slurry. Suitable coatings include surface coatings, coatings that penetrate a portion of the substrate, coatings that permeate the substrate, or some combination thereof.

A washcoat can also include non-catalytic components, such as fillers, binders, stabilizers, rheology modifiers, and other additives, including one or more of alumina, silica, non-zeolite silica alumina, titania, zirconia, ceria. The catalyst composition can comprise pore-forming agents such as graphite, cellulose, starch, polyacrylate, and polyethylene, and the like. These additional components do not necessarily catalyze the desired reaction, but instead improve the catalytic material's effectiveness, for example, by increasing its operating temperature range, increasing contact surface area of the catalyst, increasing adherence of the catalyst to a substrate, etc. Preferably, the washcoat loading is >0.3 g/in$^3$, such as >1.2 g/in$^3$, >1.5 g/in$^3$, >1.7 g/in$^3$ or >2.00 g/in$^3$, and preferably <3.5 g/in$^3$, such as <2.5 g/in$^3$. The washcoat can be applied to a substrate in a loading of about 0.8 to 1.0 g/in$^3$, 1.0 to 1.5 g/in$^3$, or 1.5 to 2.5 g/in$^3$.

Two of the most common substrate designs to which catalyst may be applied are plate and honeycomb. Preferred substrates, particularly for mobile applications, include flow-through monoliths having a so-called honeycomb geometry that comprise multiple adjacent, parallel channels that are open on both ends and generally extend from the inlet face to the outlet face of the substrate and result in a high-surface area-to-volume ratio. For certain applications, the honeycomb flow-through monolith preferably has a high cell density, for example about 600 to 800 cells per square inch, and/or an average internal wall thickness of about 0.18-0.35 mm, preferably about 0.20-0.25 mm. For certain other applications, the honeycomb flow-through monolith preferably has a low cell density of about 150-600 cells per square inch, more preferably about 200-400 cells per square inch. Preferably, the honeycomb monoliths are porous. In addition to cordierite, silicon carbide, silicon nitride, ceramic, and metal, other materials that can be used for the substrate include aluminum nitride, silicon nitride, aluminum titanate, α-alumina, mullite, e.g., acicular mullite, pollucite, a thermet such as $Al_2OsZFe$, $Al_2O_3/Ni$ or $B_4CZFe$, or composites comprising segments of any two or more thereof. Preferred materials include cordierite, silicon carbide, and alumina titanate.

Plate-type catalysts have lower pressure drops and are less susceptible to plugging and fouling than the honeycomb types, which is advantageous in high efficiency stationary applications, but plate configurations can be much larger and more expensive. A honeycomb configuration is typically smaller than a plate type, which is an advantage in mobile applications, but has higher pressure drops and plug more easily. The plate substrate can be constructed of metal, preferably corrugated metal.

In one aspect of the invention, a catalyst article is made by a process described herein. The catalyst article can be produced by a process that includes the steps of applying a metal containing calcined product formed from JMZ-1S, preferably as a washcoat, to a substrate as a layer either before or after at least one additional layer of another composition for treating exhaust gas has been applied to the substrate. The one or more catalyst layers on the substrate, including the CHA catalyst layer, are arranged in consecutive layers. As used herein, the term "consecutive" with respect to catalyst layers on a substrate means that each layer is contact with its adjacent layer(s) and that the catalyst layers as a whole are arranged one on top of another on the substrate.

The CHA catalyst can be disposed on the substrate as a first layer or zone and another composition, such as an oxidation catalyst, reduction catalyst, scavenging component, or $NO_x$ storage component, can be disposed on the substrate as a second layer or zone. As used herein, the terms "first layer" and "second layer" are used to describe the relative positions of catalyst layers in the catalyst article with respect to the normal direction of exhaust gas flow-through, past, and/or over the catalyst article. Under normal exhaust gas flow conditions, exhaust gas contacts the first layer prior to contacting the second layer. The second layer can be applied to an inert substrate as a bottom layer and the first layer is a top layer that is applied over the second layer as a consecutive series of sub-layers.

The exhaust gas can penetrate (and hence contact) the first layer, before contacting the second layer, and subsequently returns through the first layer to exit the catalyst component.

The first layer can be a first zone disposed on an upstream portion of the substrate and the second layer is disposed on the substrate as a second zone, wherein the second zone is downstream of the first.

The catalyst article can be produced by a process that includes the steps of applying JMZ-1SC, preferably as a washcoat, to a substrate as a first zone, and subsequently applying at least one additional composition for treating an exhaust gas to the substrate as a second zone, wherein at least a portion of the first zone is downstream of the second zone. Alternatively, the CHA catalyst composition can be applied to the substrate in a second zone that is downstream of a first zone containing the additional composition. Examples of additional compositions include oxidation catalysts, reduction catalysts, scavenging components (e.g., for sulfur, water, etc.), or $NO_x$ storage components.

To reduce the amount of space required for an exhaust system, individual exhaust components can be designed to perform more than one function. For example, applying an SCR catalyst to a wall-flow filter substrate instead of a flow-through substrate serves to reduce the overall size of an exhaust treatment system by allowing one substrate to serve two functions, namely catalytically reducing $NO_x$ concentration in the exhaust gas and mechanically removing soot from the exhaust gas. The substrate can be a honeycomb wall-flow filter or partial filter. Wall-flow filters are similar to flow-through honeycomb substrates in that they contain a plurality of adjacent, parallel channels. However, the channels of flow-through honeycomb substrates are open at both ends, whereas the channels of wall-flow substrates have one end capped, wherein the capping occurs on opposite ends of adjacent channels in an alternating pattern. Capping alternating ends of channels prevents the gas entering the inlet face of the substrate from flowing straight through the channel and existing. Instead, the exhaust gas enters the front of the substrate and travels into about half of the channels where it is forced through the channel walls prior to entering the second half of the channels and exiting the back face of the substrate.

The substrate wall has a porosity and pore size that is gas permeable, but traps a major portion of the particulate matter, such as soot, from the gas as the gas passes through the wall. Preferred wall-flow substrates are high efficiency filters. Wall flow filters for use with the present invention preferably have an efficiency of least 70%, at least about 75%, at least about 80%, or at least about 90%. The efficiency can be from about 75 to about 99%, about 75 to about 90%, about 80 to about 90%, or about 85 to about 95%. Here, efficiency is relative to soot and other similarly sized particles and to particulate concentrations typically found in conventional diesel exhaust gas. For example, particulates in diesel exhaust can range in size from 0.05 microns to 2.5 microns. Thus, the efficiency can be based on this range or a sub-range, such as 0.1 to 0.25 microns, 0.25 to 1.25 microns, or 1.25 to 2.5 microns.

Porosity is a measure of the percentage of void space in a porous substrate and is related to backpressure in an exhaust system: generally, the lower the porosity, the higher the backpressure. Preferably, the porous substrate has a porosity of about 30 to about 80%, for example about 40 to about 75%, about 40 to about 65%, or from about 50 to about 60%.

The pore interconnectivity, measured as a percentage of the substrate's total void volume, is the degree to which pores, void, and/or channels, are joined to form continuous paths through a porous substrate, i.e., from the inlet face to the outlet face. In contrast to pore interconnectivity is the sum of closed pore volume and the volume of pores that have a conduit to only one of the surfaces of the substrate. Preferably, the porous substrate has a pore interconnectivity volume of at least about 30%, more preferably at least about 40%.

The mean pore size of the porous substrate is also important for filtration. Mean pore size can be determined by any acceptable means, including by mercury porosimetry. The mean pore size of the porous substrate should be of a high enough value to promote low backpressure, while providing an adequate efficiency by either the substrate per se, by promotion of a soot cake layer on the surface of the substrate, or combination of both. Preferred porous substrates have a mean pore size of about 10 to about 40 μm, for example about 20 to about 30 μm, about 10 to about 25 μm, about 10 to about 20 μm, about 20 to about 25 μm, about 10 to about 15 μm, and about 15 to about 20 μm.

In general, the production of an extruded solid body, such as honeycomb flow-through or wall-flow filter, containing the catalyst JMZ-1SC involves blending JMZ-1SC, a binder, an optional organic viscosity-enhancing compound into an homogeneous paste which is then added to a binder/matrix component or a precursor thereof and optionally one or more of stabilized ceria, and inorganic fibers. The blend is compacted in a mixing or kneading apparatus or an extruder. The mixtures have organic additives such as binders, pore formers, plasticizers, surfactants, lubricants, dispersants as processing aids to enhance wetting and therefore produce a uniform batch. The resulting plastic material is then molded, in particular using an extrusion press or an extruder including an extrusion die, and the resulting moldings are dried and calcined. The organic additives are "burnt out" during calcinations of the extruded solid body. JMZ-1SC, the catalytically active calcined product, may also be washcoated or otherwise applied to the extruded solid body as one or more sub-layers that reside on the surface or penetrate wholly or partly into the extruded solid body.

The binder/matrix component is preferably selected from the group consisting of cordierite, nitrides, carbides, borides, intermetallics, lithium aluminosilicate, a spinel, an optionally doped alumina, a silica source, titania, zirconia, titania-zirconia, zircon and mixtures of any two or more thereof. The paste can optionally contain reinforcing inorganic fibers selected from the group consisting of carbon fibers, glass fibers, metal fibers, boron fibers, alumina fibers, silica fibers, silica-alumina fibers, silicon carbide fibers, potassium titanate fibers, aluminum borate fibers and ceramic fibers.

The alumina binder/matrix component is preferably gamma alumina, but can be any other transition alumina, i.e., alpha alumina, beta alumina, chi alumina, eta alumina, rho alumina, kappa alumina, theta alumina, delta alumina, lanthanum beta alumina and mixtures of any two or more such transition aluminas. It is preferred that the alumina is doped with at least one non-aluminum element to increase the thermal stability of the alumina. Suitable alumina dopants include silicon, zirconium, barium, lanthanides and mixtures of any two or more thereof. Suitable lanthanide dopants include La, Ce, Nd, Pr, Gd and mixtures of any two or more thereof.

Preferably, JMZ-1SC, the calcined product, is dispersed throughout, and preferably evenly throughout, the entire extruded catalyst body.

Where any of the above extruded solid bodies are made into a wall-flow filter, the porosity of the wall-flow filter can be from 30-80%, such as from 40-70%. Porosity and pore volume and pore radius can be measured e.g. using mercury intrusion porosimetry.

In still another aspect of the invention, provided is a method for treating an exhaust gas by contacting JMZ-1SC or a metal containing JMZ-1SC with and exhaust gas and converting a portion of ammonia and $NO_x$ in an exhaust gas into nitrogen and water.

JMZ-1SC or a metal containing JMZ-1SC can promote the reaction of a reductant, preferably ammonia, with nitrogen oxides to selectively form elemental nitrogen ($N_2$) and water ($H_2O$). Thus, the catalyst can be formulated to favor the reduction of nitrogen oxides with a reductant (i.e., an SCR catalyst). Examples of such reductants include hydrocarbons (e.g., C3-C6 hydrocarbons) and nitrogenous reductants such as ammonia and ammonia hydrazine or any suitable ammonia precursor, such as urea (($NH_2$)$_2$CO), ammonium carbonate, ammonium carbamate, ammonium hydrogen carbonate or ammonium formate.

JMZ-1SC, the calcined product formed from JMZ-1S, or a metal containing JMZ-1SC can also promote the oxidation of ammonia. Preferably, JMZ-1SC contains one or more metal ions, such as copper or iron, that are impregnated into JMZ-1SC. The catalyst can be formulated to favor the oxidation of ammonia with oxygen, particularly a concentration of ammonia typically encountered downstream of an SCR catalyst (e.g., ammonia oxidation (AMOX) catalyst, such as an ammonia slip catalyst (ASC)). The CHA catalyst can be disposed as a top layer over an oxidative under-layer, wherein the under-layer comprises a platinum group metal (PGM) catalyst or a non-PGM catalyst. Preferably, the catalyst component in the underlayer is disposed on a high surface area support, including but not limited to alumina.

SCR and AMOX operations can be performed in series, wherein both processes utilize a catalyst comprising the CHA catalyst described herein, and wherein the SCR process occurs upstream of the AMOX process. For example, an SCR formulation of the catalyst can be disposed on the inlet side of a filter and an AMOX formulation of the catalyst can be disposed on the outlet side of the filter.

Accordingly, provided is a method for the reduction of $NO_x$ compounds or oxidation of $NH_3$ in a gas, which comprises contacting the gas with a catalyst composition described herein for the catalytic reduction of $NO_x$ compounds for a time sufficient to reduce the level of $NO_x$ compounds and/or $NH_3$ in the gas. A catalyst article can have an ammonia slip catalyst disposed downstream of a selective catalytic reduction (SCR) catalyst. The ammonia slip catalyst can oxidize at least a portion of any nitrogenous reductant that is not consumed by the selective catalytic reduction process. The ammonia slip catalyst can be disposed on the outlet side of a wall flow filter and an SCR catalyst can be disposed on the upstream side of a filter. The ammonia slip catalyst can be disposed on the downstream end of a flow-through substrate and an SCR catalyst can be disposed on the upstream end of the flow-through substrate. The ammonia slip catalyst and SCR catalyst can be disposed on separate bricks within the exhaust system. These separate bricks can be adjacent to, and in contact with, each other or separated by a specific distance, provided that they are in fluid communication with each other and provided that the SCR catalyst brick is disposed upstream of the ammonia slip catalyst brick.

The SCR and/or AMOX process can be performed at a temperature of at least 100° C., preferably at a temperature from about 150° C. to about 750° C., more preferably from about 175 to about 550° C., even more preferably from 175 to 400° C.

In some conditions, the temperature range can be from 450 to 900° C., preferably 500 to 750° C., more preferably 500 to 650° C., even more preferably 450 to 550° C. Temperatures greater than 450° C. are particularly useful for treating exhaust gases from a heavy and light duty diesel engine that is equipped with an exhaust system comprising (optionally catalyzed) diesel particulate filters which are regenerated actively, e.g. by injecting hydrocarbon into the exhaust system upstream of the filter, wherein the zeolite catalyst for use in the present invention is located downstream of the filter.

According to another aspect of the invention, provided is a method for the reduction of $NO_X$ compounds and/or oxidation of $NH_3$ in a gas, which comprises contacting the gas with JMZ-1SC or a metal containing JMZ-1SC for a time sufficient to reduce the level of $NO_x$ compounds in the gas. Methods of the present invention may comprise one or more of the following steps: (a) accumulating and/or combusting soot that is in contact with the inlet of a catalytic filter; (b) introducing a nitrogenous reducing agent into the exhaust gas stream prior to contacting the catalytic filter, preferably with no intervening catalytic steps involving the treatment of $NO_x$ and the reductant; (c) generating $NH_3$ over a $NO_x$ adsorber catalyst or lean $NO_x$ trap, and preferably using such $NH_3$ as a reductant in a downstream SCR reaction; (d) contacting the exhaust gas stream with a DOC to oxidize hydrocarbon based soluble organic fraction (SOF) and/or carbon monoxide into $CO_2$, and/or oxidize NO into $NO_2$, which in turn, may be used to oxidize particulate matter in particulate filter; and/or reduce the particulate matter (PM) in the exhaust gas; (e) contacting the exhaust gas with one or more flow-through SCR catalyst device(s) in the presence of a reducing agent to reduce the NOx concentration in the exhaust gas; and (f) contacting the exhaust gas with an ammonia slip catalyst, preferably downstream of the SCR catalyst to oxidize most, if not all, of the ammonia prior to emitting the exhaust gas into the atmosphere or passing the exhaust gas through a recirculation loop prior to exhaust gas entering/re-entering the engine.

All, or at least a portion of, the nitrogen-based reductant, particularly $NH_3$, for consumption in the SCR process can be supplied by a $NO_X$ adsorber catalyst (NAC), a lean $NO_X$ trap (LNT), or a $NO_X$ storage/reduction catalyst (NSRC), disposed upstream of the SCR catalyst, e.g., a SCR catalyst of the present invention disposed on a wall-flow filter. NAC components useful in the present invention include a catalyst combination of a basic material (such as alkali metal, alkaline earth metal or a rare earth metal, including oxides of alkali metals, oxides of alkaline earth metals, and combinations thereof), and a precious metal (such as platinum), and optionally a reduction catalyst component, such as rhodium. Specific types of basic material useful in the NAC include cesium oxide, potassium oxide, magnesium oxide, sodium oxide, calcium oxide, strontium oxide, barium oxide, and combinations thereof. The precious metal is preferably present at about 10 to about 200 g/ft$^3$, such as 20 to 60 g/ft$^3$. Alternatively, the precious metal of the catalyst is characterized by the average concentration which may be from about 40 to about 100 grams/ft$^3$.

During periodically rich regeneration events, $NH_3$ may be generated over a $NO_x$ adsorber catalyst. The SCR catalyst downstream of the $NO_x$ adsorber catalyst may improve the overall system $NO_x$ reduction efficiency. In the combined system, the SCR catalyst is capable of storing the released $NH_3$ from the NAC catalyst during rich regeneration events and utilizes the stored $NH_3$ to selectively reduce some or all of the $NO_x$ that slips through the NAC catalyst during the normal lean operation conditions.

The method for treating exhaust gas as described herein can be performed on an exhaust gas derived from a combustion process, such as from an internal combustion engine (whether mobile or stationary), a gas turbine and coal or oil fired power plants. The method may also be used to treat gas from industrial processes such as refining, from refinery heaters and boilers, furnaces, the chemical processing industry, coke ovens, municipal waste plants and incinerators, etc. The method can be used for treating exhaust gas from a vehicular lean burn internal combustion engine, such as a diesel engine, a lean-burn gasoline engine or an engine powered by liquid petroleum gas or natural gas.

In certain aspects, the invention is a system for treating exhaust gas generated by combustion process, such as from an internal combustion engine (whether mobile or stationary), a gas turbine, coal or oil fired power plants, and the like. Such systems include a catalytic article comprising JMZ-1SC, described herein, and at least one additional component for treating the exhaust gas, wherein the catalytic article and at least one additional component are designed to function as a coherent unit.

A system can comprise a catalytic article comprising JMZ-1SC or a metal containing JMZ-1SC, a conduit for directing a flowing exhaust gas, and a source of nitrogenous reductant disposed upstream of the catalytic article. The system can include a controller for metering the nitrogenous reductant into the flowing exhaust gas only when it is determined that JMZ-1SC or a metal containing JMZ-1SC is capable of catalyzing $NO_x$ reduction at or above a desired efficiency over a specific temperature range, such as at above 100° C., above 150° C. or above 175° C. The metering of the nitrogenous reductant can be arranged such that 60% to 200% of theoretical ammonia is present in exhaust gas entering the SCR catalyst calculated at 1:1 $NH_3$/NO and 4:3 $NH_3$/$NO_2$.

The system can comprise an oxidation catalyst (e.g., a diesel oxidation catalyst (DOC)) for oxidizing nitrogen monoxide in the exhaust gas to nitrogen dioxide can be located upstream of a point of metering the nitrogenous reductant into the exhaust gas. The oxidation catalyst can be adapted to yield a gas stream entering the SCR zeolite catalyst having a ratio of NO to $NO_2$ of from about 4:1 to about 1:3 by volume, e.g. at an exhaust gas temperature at oxidation catalyst inlet of 250° C. to 450° C. The oxidation catalyst can include at least one platinum group metal (or some combination of these), such as platinum, palladium, or rhodium, coated on a flow-through monolith substrate. The at least one platinum group metal can be platinum, palladium or a combination of both platinum and palladium. The platinum group metal can be supported on a high surface area washcoat component such as alumina, a zeolite such as an silicoaluminophosphate zeolite, silica, non-zeolite silica alumina, ceria, zirconia, titania or a mixed or composite oxide containing both ceria and zirconia.

A suitable filter substrate can be located between the oxidation catalyst and the SCR catalyst. Filter substrates can be selected from any of those mentioned above, e.g. wall flow filters. Where the filter is catalyzed, e.g. with an oxidation catalyst of the kind discussed above, preferably the point of metering nitrogenous reductant is located between the filter and the zeolite catalyst. Alternatively, if the filter is un-catalyzed, the means for metering nitrogenous reductant can be located between the oxidation catalyst and the filter.

JMZ-1SC or a metal containing JMZ-1SC can also promote the formation of methylamines from the reaction of methanol and ammonia and the conversion of methanol to lower olefins, especially ethylene and propylene.

A method of converting an oxygenate, such as methanol, to an olefin (MTO) by contacting methanol with JMZ-1SC or a metal containing JMZ-1SC as herein before described. The reaction process for the conversion of an oxygenate to olefin (OTO) is well known in the art. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene.

A process for converting an oxygenate feed to a light olefin product comprises: a) providing an oxygenate feed comprising a majority of methanol; b) providing a catalyst composition comprising JMZ-1SC or a metal containing JMZ-1SC and optionally a basic metal oxide co-catalyst; and c) contacting the oxygenate feed with the catalyst composition under conditions sufficient to convert at least a portion of the oxygenate feed to a light olefin product.

An oxygenate feedstock, particularly a mixed alcohol composition containing methanol and ethanol, is a useful feedstock for a variety of catalytic processes, particularly oxygenate to olefin (OTO) reaction processes, in which a catalyst composition, typically containing a primary oxide catalyst having at least two of Al, Si, and P (e.g., an silicoaluminophosphate molecular sieve) and preferably a basic metal oxide co-catalyst, can be used to convert the oxygenate feedstock into a light olefin product, e.g., containing ethylene and/or propylene, preferably including ethylene. The olefins can then be recovered and used for further processing, e.g., in the manufacture of polyolefins such as polyethylene and/or polypropylene, olefin oligomers, olefin copolymers, mixtures thereof, and/or blends thereof.

One or more additional components can be included in the feedstock that is directed to the OTO reaction system. For example, a feedstock directed to the OTO reaction system can optionally contain, in addition to methanol and ethanol, one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to 50 carbon atoms, preferably from 1 to 20 carbon atoms, more preferably from 1 to 10 carbon atoms, most preferably from 1 to 4 carbon atoms.

Non-limiting examples of aliphatic-containing compounds include: alcohols such as methanol, ethanol, n-propanol, isopropanol, and the like, alkyl-mercaptans such as methyl mercaptan and ethyl mercaptan, alkyl-sulfides such as methyl sulfide, alkyl amines such as methyl amine, alkyl ethers such as DME, diethyl ether and methyl ethyl ether, alkyl-halides such as methyl chloride and ethyl chloride, alkyl ketones such as dimethyl ketone, alkyl-aldehydes such as formaldehyde and acetaldehyde, and various organic acids such as formic acid and acetic acid.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene. Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomers can include, but are not limited to, unsaturated monomers, diolefins having 4 to 18 carbon atoms, conjugated or non-conjugated dienes, polyenes, vinyl monomers, and cyclic olefins.

A catalyst article for converting a low molecular weight oxygen containing species to an olefin rich hydrocarbon stream can comprise JMZ-1SC or a metal containing JMZ-1SC, where JMZ-1SC or a metal containing JMZ-1SC is disposed on a support and/or within a structure.

A catalyst article for converting a low molecular weight oxygen containing species to an aromatic rich hydrocarbon stream can comprise JMZ-1SC or a metal containing JMZ-1SC, where JMZ-1SC or a metal containing JMZ-1SC is disposed on a support and/or within a structure.

The catalyst can be incorporated or mixed with other additive materials. Such an admixture is typically referred to as formulated catalyst or as catalyst composition. Preferably, the additive materials are substantially inert to conversion reactions involving dialkyl ethers (e.g., dimethyl ether) and/or alkanols (e.g., methanol, ethanol, and the like).

One or more other materials can be mixed with JMZ-1SC or a metal containing JMZ-1SC, particularly a material that is resistant to the temperatures and other conditions employed in organic conversion processes. Such materials can include catalytically active and inactive materials and synthetic or naturally occurring zeolites, as well as inorganic materials such as clays, silica, and/or other metal oxides such as alumina. The latter may be either naturally occurring or in the form of gelatinous precipitates or gels including mixtures of silica and metal oxides. Use of a catalytically active material can tend to change the conversion and/or selectivity of the catalyst in the oxygenate conversion process. Inactive materials suitably can serve as diluents to control the amount of conversion in the process so that products can be obtained in an economic and orderly manner without employing other means for controlling the rate of reaction. These materials can be incorporated into naturally occurring clays, e.g., bentonite and kaolin, to improve the crush strength of the catalyst under commercial operating conditions. The materials (e.g., clays, oxides, etc.) can function as binders for the catalyst. It can be desirable to provide a catalyst having good crush strength, because, in commercial use, it can be desirable to prevent the catalyst from breaking down into powder-like materials.

Naturally occurring clays that can be employed can include, but are not limited to, the montmorillonite and kaolin family, which families include the subbentonites, and the kaolins commonly known as Dixie, McNamee, Georgia and Florida clays, or others in which the main mineral constituent includes halloysite, kaolinite, dickite, nacrite, or anauxite. Such clays can be used in the raw state as originally mined or initially subjected to calcination, acid treatment, or chemical modification. Other useful binders can include, but are not limited to, inorganic oxides such as silica, titania, beryllia, alumina, and mixtures thereof.

In addition to the foregoing materials, JMZ-1SC or a metal containing JMZ-1SC can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The relative proportions of JMZ-1SC or a metal containing JMZ-1SC and an inorganic oxide matrix can vary widely. For example, a mixture can include a zeolite content ranging from about 1 to about 90 percent by weight and more usually, particularly when the composite is prepared in the form of beads, in the range from about 2 to about 80 weight percent of the composite.

The invention also relates to C2, C3, C4 and C5 products formed by OTO or MTO application using JMZ-1SC or a metal containing JMZ-1SC as a catalyst or co-catalyst.

EXAMPLES

Example 1. Synthesis of Zeolite JMZ-1S

A reaction gel having a molar composition:
0.50 $SiO_2$:1 $Al_2O_3$:0.75 $P_2O_5$:0.80 Template:90 $H_2O$
was prepared by weighing the individual reagents into a PTFE cup containing a PTFE magnetic follower (stir bar). The reagents used, and their order of addition, was:
 a) De-mineralised water,
 b) Phosphoric Acid, c) Silica Fumed,
d) Aluminum Hydroxide,
e) Template—Trimethyl(cyclohexylmethyl)ammonium hydroxide.

Approximately 4% w/w of SAPO-34 seeds based on the weight of solid silica used as a reagent was added to the reaction mixture. After all the reagents had been added, the mixture was homogenised over a 60 minutes period at room temperature. The PTFE cup was placed in a stainless steel outer vessel, sealed, then placed in an oven at 210° C. with rotation at 45 rpm and the reagents in the mixture were reacted. After 24 hours at 210° C., the oven was cooled, the reactor was opened and the resulting material was subjected to centrifugation, decantation and addition of de-mineralised water. After the initial mixing with water and the removal of the water, the procedure was repeated 3 additional times (4 washes in total) following which resulting product was dried overnight at 110° C.

Figure 1:
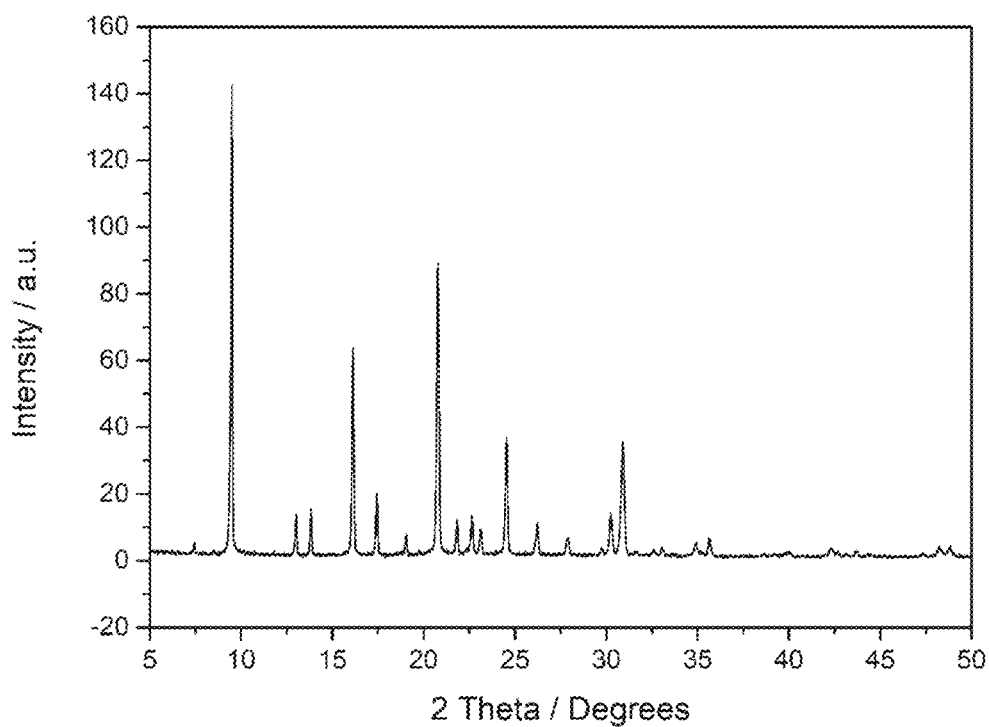
FIG. 1 is an XRD spectra of a sample containing a mixture of approximately 95% w/w of JMZ-1S and 5% w/w of a zeolite having an AFI-framework, as prepared in Example 1.

Analysis of the dried powder by powder XRD indicated that the product was a mixture of zeolite JMZ-1S (approximately 95% w/w) and a zeolite having an AFI-type phase (approximately 5% w/w). The powder XRD pattern is shown in FIG. 1.

Example 2. Synthesis of Zeolite JMZ-1S

A reaction gel having a molar composition:
0.50 SiO$_2$:1 Al$_2$O$_3$:1 P$_2$O$_5$:1.20 Template:90 H$_2$O
was prepared by weighing the individual reagents into a PTFE cup containing a PTFE magnetic follower (stir bar). The reagents used, and their order of addition, was:
a) De-mineralised water,
b) Phosphoric Acid,
c) Silica Fumed,
d) Aluminum Hydroxide,
e) Template—Trimethyl(cyclohexylmethyl)ammonium hydroxide.

A portion of the product from Example 1 (approximately 4% w/w based on the weight of solid silica used as a reagent) was added to the reaction mixture. The reaction mixture was homogenised as described in Example 1, then reacted for 24 hours at 210° C. while rotating the reactor at 45 rpm.

Figure 2:
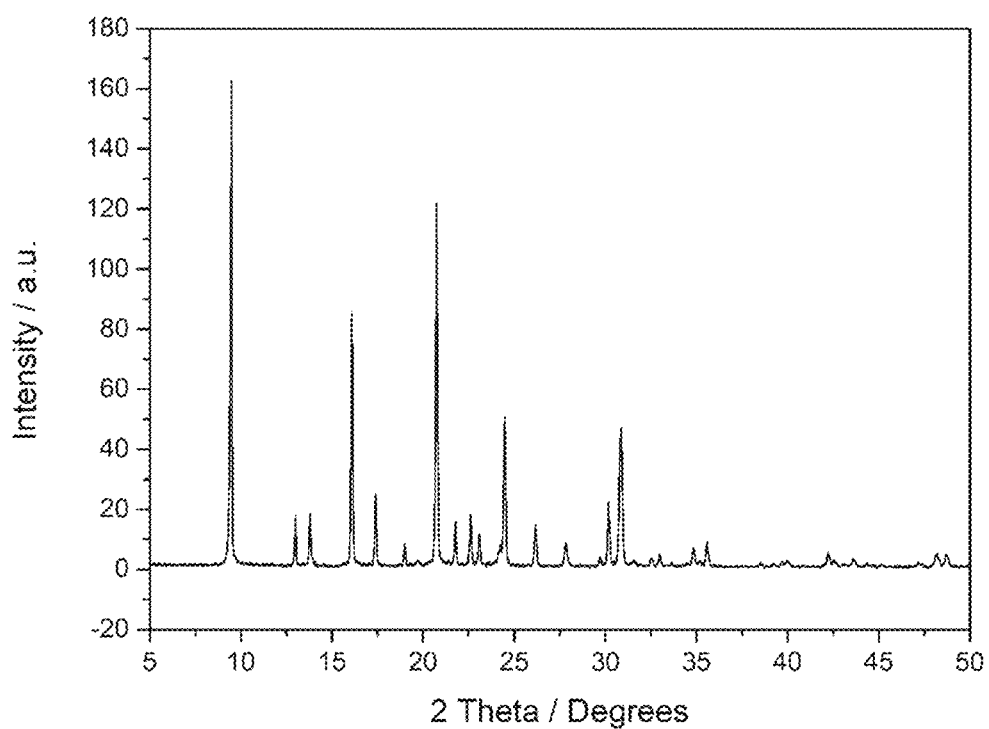
FIG. 2 is an XRD spectra of a sample of JMZ-1S as prepared in Example 2.

The product was treated as described in Example 1, then analysed by powder XRD. The product comprised phase-pure zeolite JMZ-1S. The powder XRD pattern is shown in FIG. 2 and the lines in the XRD spectra are shown in Table 1.

TABLE 1

Powder XRD characteristic lines for as-made (template containing) JMZ-1S molecular sieve. Peaks with the relative intensities, 100 I/I$_0$ ≤ 4 are not listed in the table.

| Degrees two-theta | I/Io |
|---|---|
| 9.47 | VS |
| 12.99 | W |
| 13.80 | W |
| 16.09 | S |
| 17.39 | W |
| 18.99 | W |
| 20.74 | VS |
| 21.78 | W |
| 22.61 | W |
| 23.09 | W |
| 24.49 | M |
| 26.16 | W |
| 27.84 | W |
| 30.20 | W |

TABLE 1-continued

Powder XRD characteristic lines for as-made (template containing) JMZ-1S molecular sieve. Peaks with the relative intensities, 100 I/I$_0$ ≤ 4 are not listed in the table.

| Degrees two-theta | I/Io |
|---|---|
| 30.85 | M |
| 34.84 | W |
| 35.61 | W |

Table 2 shows a comparison of the characteristic lines of powder XRD of JMZ-1S with those of SAPO-34 (CHA containing SDA) taken from table Q in U.S. Pat. No. 4,440,871.

TABLE 2

Powder XRD characteristic lines for JMZ-1S (template containing) compared to Uncalcined SAPO-34 (template containing).

| JMZ-1S | | SAPO-34 | |
|---|---|---|---|
| Degrees two-theta | I/Io | Degrees two-theta | I/Io |
| 9.47 | 100 | 9.6 | 100 |
| 12.99 | 9 | 13.0 | 17 |
| 13.80 | 11 | 14.05 | 23 |
| 16.09 | 50 | 16.1 | 33 |
| 17.39 | 15 | 17.85 | 75 |
| 18.99 | 4 | 19.0 | 2 |
| 20.74 | 75 | 20.7 | 99 |
| 21.78 | 9 | 22.05 | 4 |
| 22.61 | 10 | | |
| 23.09 | 6 | 23.1 | 10 |
| 24.49 | 30 | 24.95 | 76 |
| 26.16 | 8 | 26.0 | 19 |
| 27.84 | 5 | 27.7 | 3 |
| 29.71 | 1 | 29.4 | 4 |
| 30.20 | 13 | 30.7 | 67 |
| 30.85 | 27 | 31.05 | 28 |
| 32.53 | 2 | 32.4 | 2 |
| 32.99 | 2 | 33.4 | 6 |
| 34.84 | 22 | 34.55 | 14 |
| 35.61 | 44 | 36.0 | 11 |

This comparison shows that although both JMZ-1S and SAPO-34 are template containing zeolites having a CHA structure, the structure of the two materials is different.

Example 3. Synthesis of Zeolite JMZ-1S

A reaction gel having a molar composition:
0.60 SiO$_2$:1 Al$_2$O$_3$:0.90 P$_2$O$_5$:1.0 Template:90 H$_2$O
was prepared by weighing the individual reagents into a PTFE cup containing a PTFE magnetic follower (stir bar). The reagents used, and their order of addition, was:
a) De-mineralised water,
b) Phosphoric Acid,
c) Silica Fumed,
d) Aluminum Hydroxide,
e) Template—Trimethyl(cyclohexylmethyl)ammonium hydroxide.

A portion of the product from Example 3 (approximately 4% w/w based on the weight of solid silica used as a reagent) was added to the reaction mixture. The reaction mixture was homogenised as described in Example 1, then reacted for 24 hours at 210° C. while rotating the reactor at 45 rpm.

The product was treated as described in Example 1, then analysed by powder XRD. The product comprised phase-pure zeolite JMZ-1S. The powder XRD pattern is shown in FIG. 3 and the lines in the XRD spectra are shown in Table 3. The SEM image of the material is shown is FIG. 4.

Figure 5:
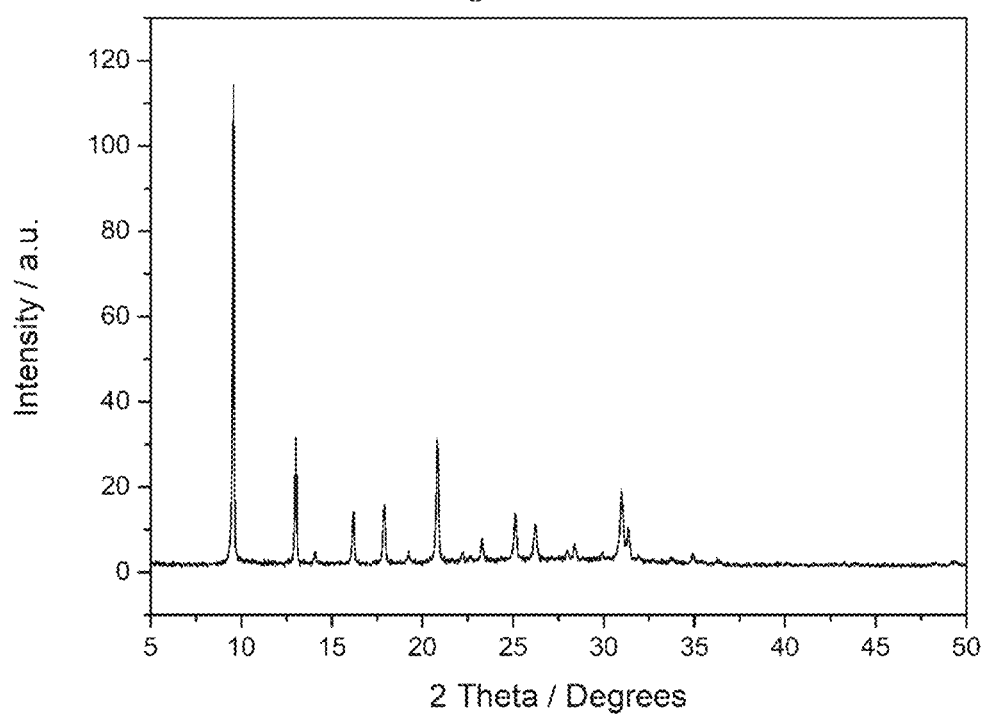
FIG. 5 is an XRD spectra of a sample of calcined JMZ-1S (JMZ-1SC) as prepared in Example 3.

The as-made zeolite (JMZ-1S) was activated by calcining in air. The sample was heated to 110° C. at 2° C./min then heated to 450° C. at 5° C./min and held at 450° C. for 16 hours. The material was then heated to 550° C. at 5° C./min at held at 550° C. for 16 hours. The product after activation had an XRD powder pattern as shown in FIG. 5 and contained the interplanar spacings and intensities shown in Table 4.

TABLE 3

Powder XRD characteristic lines for as-made (template containing) JMZ-1S molecular sieve. Peaks with the relative intensities, 100 I/Io ≤ 4 are not listed in the table.

| Degrees two-theta | I/Io |
| --- | --- |
| 9.47 | VS |
| 12.99 | W |
| 13.81 | W |
| 16.10 | S |
| 17.41 | W |
| 19.01 | W |
| 20.73 | VS |
| 21.80 | W |
| 22.60 | W |
| 23.09 | W |
| 24.51 | M |
| 26.15 | W |
| 27.86 | W |
| 30.22 | W |
| 30.86 | M |
| 34.84 | W |
| 35.63 | W |

TABLE 4

Powder XRD characteristic lines for activated (template-free) JMZ-1S molecular sieve. Peaks with the relative intensities, 100 I/Io ≤ 4 are not listed in the table.

| Degrees two-theta | I/Io |
| --- | --- |
| 9.57 | VS |
| 13.01 | M |
| 16.17 | W |
| 17.89 | W |
| 20.82 | M |
| 23.29 | W |
| 25.12 | W |
| 26.22 | W |
| 30.99 | W |
| 31.34 | W |

What is claimed is:

1. A molecular sieve comprising a CHA type framework type with phosphate within the framework, wherein the molecular sieve is silicoaluminophosphate, the molecular sieve having a $SiO_2/Al_2O_3$ (SAR) of between 0.45 and 0.55 inclusive, and a $P_2O_5/Al_2O_3$ (PAR) ratio of between 0.75 and 0.85 inclusive.

2. The molecular sieve of claim 1, where the molecular sieve further comprises at least one extra-framework transition metal selected from the group consisting of Ag, Au, Ce, Co, Cr, Cu, Fe, Ga, In, Ir, Mn, Mo, Nb, Ni, Pd, Pt, Re, Rh, Ru, Sn, Ta, V, W and Zn.

3. The molecular sieve of claim 1, where the molecular sieve is calcined or contains one or more structure directing agents (SDAs).

4. A molecular sieve of claim 1, comprising a CHA type framework type molecular sieve containing a structure directing agent (SDA) having a characteristic X-ray powder diffraction pattern comprising 2-theta positions at 9.47 (VS), 16.10 (S), 20.73 (VS), 24.51 (M) and 30.86 (M)±0.2 with the corresponding relative intensity shown in parenthesis.

5. A molecular sieve of claim 4, wherein the characteristic X-ray powder diffraction pattern further comprises 2-theta positions at 12.99 (W), 13.81 (W), 17.41 (W), 19.01 (W), 21.80 (W), 22.60 (W), 23.09 (W), 26.15 (W), 27.86 (W), 30.22 (W), 34.84 (W), 35.63 (W)±0.2 with the corresponding relative intensity shown in parenthesis.

6. The molecular sieve of claim 1 prepared by using a structure-directing agent comprising trimethyl(cyclohexylmethyl) ammonium cations.

7. A composition comprising a silicoaluminophosphate molecular sieve crystal having a CHA framework, as synthesized and in an anhydrous state, comprising a pentavalent phosphorus oxide, a trivalent aluminum oxide, a tetravalent silicon oxide, and having a trimethyl(cyclohexylmethyl) ammonium cation present in the crystal structure, wherein the molecular sieve crystal is free of substituted or unsubstituted 5,4-azonium anions and is free of ammonium anions having a substituents selected from bridged polycyclics, cycloaryls, heterocyclics, cycloalkyls other than cyclohexylmethyl, and C2-C4 alkyls.

8. A calcined zeolite comprising a framework structure comprising a CHA type framework with phosphate within the framework, where the molecular sieve is a silicoaluminophosphate, the molecular sieve having a $SiO_2/Al_2O_3$ (SAR) of between 0.45 to 0.55 inclusive, a $P_2O_5/Al_2O_3$ (PAR) ratio of between 0.75 to 0.85 inclusive, and having a characteristic X-ray powder diffraction pattern comprising 2-theta positions at 9.57 (VS), 13.01 (M), 16.17 (W), 17.89 (W), 20.82 (M), 23.29 (W), 25.12 (W), 26.22 (W), 30.99 (W), 31.34 (W)±0.2 with the corresponding relative intensity shown in parenthesis, wherein the zeolite does not comprise a structure directing agent (SDA).

9. The calcined molecular sieve of claim 8 wherein the calcined molecular sieve further comprises an exchanged metal.

10. The calcined molecular sieve of claim 9, where the exchanged metal is copper or iron.

11. The calcined molecular sieve of claim 9 where the exchanged metal is copper.

12. A catalyst comprising a calcined molecular sieve according to claim 9.

13. The catalyst of claim 12, wherein the calcined molecular sieve further comprises a non-framework transition metal or noble metal.

14. The catalyst of claim 13, wherein the non-framework transition metal is selected from the group consisting of Cu, Fe, V, Co, Ni, Nb, Mo, Ta, Mn and W.

15. The catalyst of claim 13, wherein the non-framework transition metal is Cu or Fe.

16. The catalyst of claim 13, wherein the molecular sieve comprises about 0.1 to about 5 weight percent of the transition metal or noble metal.

17. The catalyst of claim 13, wherein the molecular sieve comprises about 0.1 to about 5 weight percent ionic copper.

18. The catalyst of claim 13, wherein the noble metal is selected from Pt, Pd, Ru, Rh, Os, Ir, Ag, or Au.

19. The catalyst of claim 13, further comprising Ca.

20. The catalyst of claim 13, further comprising Ce.

21. A catalyst article for treating exhaust gas comprising a catalyst of claim 12 disposed on and/or within a honeycomb structure.

22. A method for synthesizing a molecular sieve of claim 1, the method comprising:
a. forming heating a reaction mixture comprising: (a) at least one source of phosphate, (b) at least one source of alumina, (c) at least one source of silica, and (c) a structure directing agent (SDA) comprising trimethyl (cyclohexylmethyl) ammonium cation: and b. forming molecular sieve crystals having a CHA framework and the structure directing agent, and c. recovering at least a portion of the molecular sieve crystals from the mother liquor.

23. The method of claim 22, wherein the SDA is associated with an anion selected from the group consisting of fluoride, chloride, bromide, iodide, hydroxide, acetate, sulfate, tetrafluoroborate, carboxylate, carbonate and bicarbonate.

24. The method of claim 22, wherein the SDA is associated with an hydroxide anion.

25. The method of claim 22, wherein the reaction mixture is a gel having a molar compositional ratio of:

| | |
|---|---|
| $P_2O_5/Al_2O_3$ | 0.5-1 |
| $SiO_2/Al_2O_3$ | 0.2-0.8 |
| $SDA/Al_2O_3$ | 0.1-1.50 |
| $H_2O/Al_2O_3$ | 20-200 | wherein R is the SDA.

26. The method of claim 22, wherein the reaction mixture further comprises from about 0.1 to about 10% w/w of seed crystals, wherein the seed crystals comprise a crystalline molecular sieve having a CHA framework.

27. The method of claim 26, wherein the seed crystals comprise from 1 to 40 weight percent of at least one crystalline molecular sieve impurity.

28. A composition prepared by the method of claim 22 for synthesizing a molecular sieve of claim 1, the method comprising:

a. forming heating a reaction mixture comprising: (a) at least one source of phosphate, (b) at least one source of alumina, (c) at least one source of silica, and (d) a structure directing agent (SDA) comprising trimethyl (cyclohexylmethyl) ammonium cation: and b. forming molecular sieve crystals having a CHA framework and the structure directing agent, and recovering at least a portion of the molecular sieve crystals from the mother liquor.

29. A method for treating an exhaust gas comprising contacting a combustion exhaust gas containing $NO_x$ and/or $NH_3$ with a catalyst according to claim 12 to selectively reduce at least a portion of the $NO_x$ into $N_2$ and $H_2O$ and/or oxidize at least a portion of the $NH_3$.

30. A method of converting methanol to an olefin (MTO), the method comprising contacting methanol with a catalyst according to claim 12.

31. The molecular sieve of claim 3 wherein the molecular sieve contains a structure directing agent (SDA) which comprises trimethyl (cyclohexylmethyl) ammonium cation.

* * * * *